United States Patent [19]

Tsuchida et al.

[11] 4,451,350
[45] May 29, 1984

[54] SENSOR FOR MEASURING DENSITY OF OXYGEN IN MOLTEN METAL

[75] Inventors: Yutaka Tsuchida; Mikio Mugita, both of Fukuyama; Yutaka Nakano, Funahashi; Naoaki Sasaki, Tokyo; Kenki Ishizawa, Bizen; Hiroshi Kuroshima, Okayama, all of Japan

[73] Assignees: Nippon Kokan Kabushiki Kaisha, Tokyo; Osaka Oxygen Industries Ltd., Osaka; Shinagawa Shirorenga Kabushiki Kaisha, Tokyo, all of Japan

[21] Appl. No.: 367,227

[22] PCT Filed: Sep. 3, 1981

[86] PCT No.: PCT/JP81/00214

§ 371 Date: Mar. 29, 1982

§ 102(e) Date: Mar. 29, 1982

[87] PCT Pub. No.: WO82/00892

PCT Pub. Date: Mar. 18, 1982

[30] Foreign Application Priority Data

Sep. 5, 1980 [JP] Japan ................. 55-122412

[51] Int. Cl.³ ........................... G01N 27/58
[52] U.S. Cl. ........................ 204/422; 204/423
[58] Field of Search ............ 204/195 S, 1 S, 422, 204/423; 429/191, 193, 30, 33

[56] References Cited

U.S. PATENT DOCUMENTS

| 3,698,955 | 10/1972 | Lilly et al. | 204/195 S X |
| 3,764,269 | 10/1973 | Oldham et al. | 204/195 S X |
| 3,809,639 | 5/1974 | Faurschou et al. | 204/195 S |
| 3,837,920 | 9/1974 | Liang et al. | 429/191 |
| 4,177,112 | 12/1979 | Suzuki et al. | 204/1 S |
| 4,216,279 | 8/1980 | Mellors | 429/191 |

FOREIGN PATENT DOCUMENTS

| 48-88994 | 11/1973 | Japan | 204/195 S |
| 51-41596 | 4/1976 | Japan | 204/195 S |
| 54-2838230 | 3/1979 | Japan | 204/195 S |
| 54-150191 | 11/1979 | Japan | 204/195 S |
| 55-26405 | 2/1980 | Japan | 204/195 S |
| 55-152454 | 11/1980 | Japan | 204/195 S |
| 55-170661 | 12/1980 | Japan | 204/195 S |
| 56-168152 | 12/1981 | Japan | 204/195 S |

OTHER PUBLICATIONS

Rapp et al., Techniques of Metals Research, vol. 4, Physicochemical Measurements in Metals Research, Part 2, 1970, pp. 132-135.

Primary Examiner—G. L. Kaplan
Assistant Examiner—Nam X. Nguyen
Attorney, Agent, or Firm—Frishauf, Holtz, Goodman & Woodward

[57] ABSTRACT

A sensor comprising a solid electrolytic having oxygen ion conductivity to measure the amount of oxygen in molten metal by forming an oxygen concentration cell in which the solid electrolytic element is coated on the surface thereof with mixture which is composed of $Al_2O_3$ powders and metallic fluoride powders such as $MgF_2$ or $CaF_2$.

The present coating does not exfoliate at immersing the sensor into the molten metal and fully maintains wettability of the solid electrolytic element 1 and the molten metal, and since it does not hinder oxygen ion conductivity of the solid electrolytic element 1, the sensor rapidly reaches up to the thermal and electrical equilibrium state, thereby to obtain satisfactory emf wave.

11 Claims, 11 Drawing Figures $a_0$ = 94 PPM (CELL EMF 112 mV BATH TEMP 1600°C)
50 Kg HIGH FREQUENCY INDUCTION FURNACE
(Fe-C-O MOLTEN STEEL)

$a_O$ = 102 PPM (CELL EMF 118mV BATH TEMP 1601°C)
50Kg HIGH FREQUENCY INDUCTION FURNACE
(Fe-C-O MOLTEN STEEL)

$a_O$ = 94PPM (CELL EMF 112mV BATH TEMPERATURE 1600°C)
50Kg HIGH FREQUENCY INDUCTION FURNACE
(Fe-C-O MOLTEN STEEL)

$a_0$ = 96PPM (CELL EMF 113mV BATH TEMP 1601°C)
50Kg HIGH FREQUENCY INDUCTION FURNACE
(Fe-C-O MOLTEN STEEL)

$a_0$ = 97PPM (CELL EMF 117mV BATH TEMP 1597°C)
50Kg HIGH FREQUENCY INDUCTION FURNACE
(Fe-C-O MOLTEN STEEL)

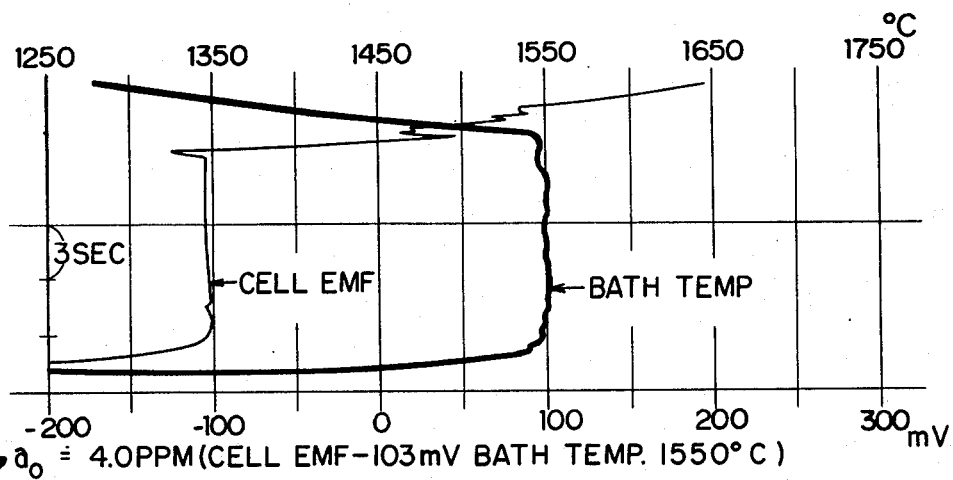
FIG. 7 $a_0$ = 4.0PPM (CELL EMF-103mV BATH TEMP. 1550°C)
300 TON LADLE AI-KILLED STEEL)
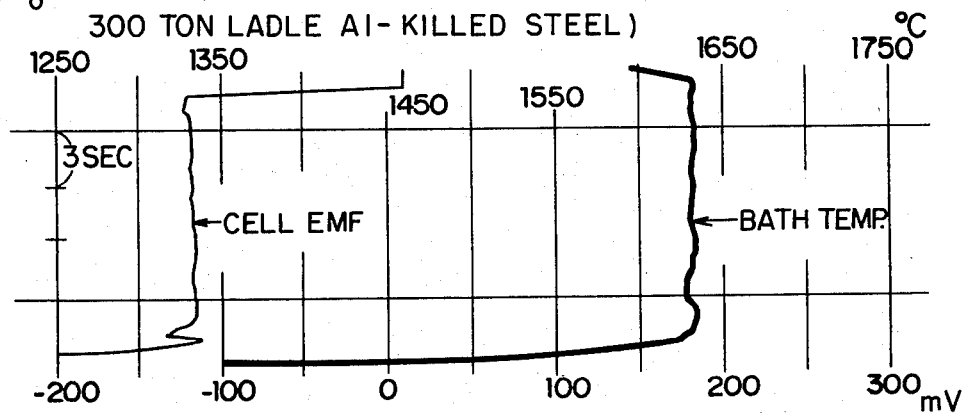
FIG. 8 $a_0$ = 7.5PPM (CELL EMF-117mV BATH TEMP. 1633°C)
250 TON LADLE (RH DEGASIFYING DEVICE AIO KILLED STEEL)
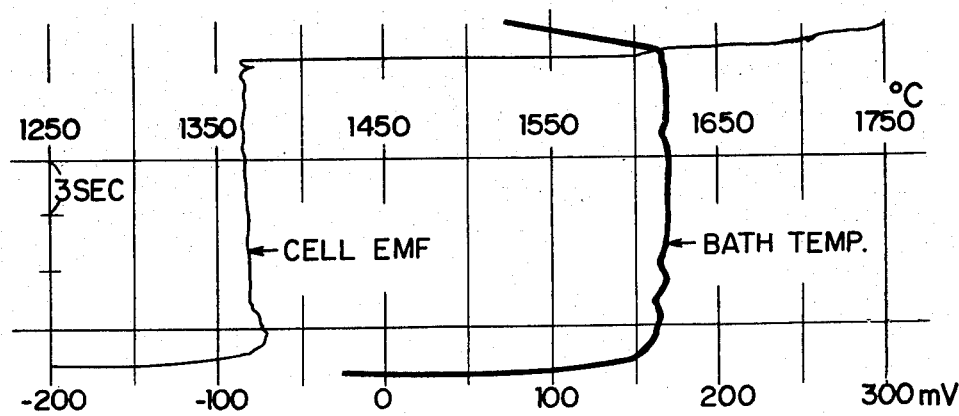
FIG. 9 $a_0$ = 10.0PPM (CELL EMF-84mV BATH TEMP. 1620°C)
250 TON LADLE (RH DEGASIFYING DEVICE AI-KILLED STEEL)

SENSOR FOR MEASURING DENSITY OF OXYGEN IN MOLTEN METAL

TECHNICAL FIELD

This invention relates to an improvement of a sensor for measuring density of oxygen in molten metal such as steel, copper and others, in which an oxygen concentration cell is generated by means of solid electrolytic element having oxygen ion conductivity.

BACKGROUND ART

Since the density of oxygen in the molten metal effects the quality of product, oxygen is a very important control ingredient. As development of the solid electrolyte has been advanced, there has recently been practised such a manner which measures the density of oxygen by directly immersing a sensor composing an oxygen concentration cell as an element of the solid electrolyte into the molten metal.

The cell is, as shown in FIG. 1, composed of Mo pole 5—molten steel—solid electrolyte 1—standard pole 3—Mo pole 4, and this composition utilizes generation of electromotive force (emf) in proportion to difference in partial pressure of oxygen, between both Mo poles. For the standard pole 3, such mixture is in general used as Ni+NiO, Mo+MoO$_2$, Cr+Cr$_2$O$_3$ and others. For the oxygen ion conductive solid electrolyte 1, a formation of a certain shape is used of metallic oxides as ZrO$_2$ radical or TiO$_2$ radical. Further the temperature of the molten metal can be concurrently measured with a thermocouple 6 incorporated in the sensor (with respect to others in FIG. 1, 7 is a ceramic housing, 8 is a connector, 9 is an iron-made cap, 10 is a ceramic fiber refractory sleeve and 11 is a paper sleeve). Herein, if an object to be measured is the molten steel, the content of of molten oxygen may be obtained in calculation with following expression by the Nernst's formula.

$$\log a_0 = \frac{10.08E - 13580}{T} + 8.62$$

(Standard pole is Cr + Cr$_2$O$_3$)

wherein;
a$_0$: Density of molten oxygen (ppm)
E: Electromotive force (mV)
T: Temperature (K)

There have been many proposals for shapes of the sensors. If measuring were carried out to determine the amount of oxygen in the molten steel by means of such a sensor where the standard pole substance 3 is, as shown in FIG. 1, filled in the solid electrolytic element 1 closing its one end (called as "element" hereafter), wave of electromotive force thereby would show an action which generates a large peak at standing due to thermal and electrical transient phenomenon as shown in FIG. 2, and changes into an equilibrium state. Herein, the ordinate in FIG. 2 designates passing time, one interval being 9 seconds, and the abscissa thereof shows the temperature of the steel bath and electromotive force. The value of "a$_0$" thereunder is obtained by substituting into the Nernst's formula the value in parentheses ( ) when the wave of electromotive force reaches up to the equilibrium state (the same in FIGS. 3 to 9).

This fact depends upon the cause that, just after immersion, large difference in temperature arises between the inner and outer surfaces of the element, whereby it takes long time for the partial pressure of dissociated oxygen of the standard pole having temprature reliance filled in the element to reach the equilibrium partial pressure.

Already known is such a sensor where the element has a coating agent 2 on its surface for providing satisfactory wettability with the molten steel in order that emf controls the peak at the low level when the wave stands to shorten the time until it reaches the equilibrium state. For the characteristics of the coating agent, the requirements are:

(1) not generating crackings or exfoliation if it were immersed into the molten steel from the room temperature, and (2) not obstructing the oxygen ion conductivity of the element.

However, the conventional coating agent of combination of Al$_2$O$_3$ powder and organic powder does not pay careful attention to the above (1) item. Just after immersion into the molten steel, cracking is created due to thermal shock, and the coating layer is exfoliated in a short period of time and the element is exposed so that the wettability with the molten steel is not fully kept, and its effect is poor. This is because the organic binder may secure combination among Al$_2$O$_3$ powder and adhesion with the element at the room temperature, but the coating agent is burnt at the same time as the immersion and loses its effect. This advantage is inevitable as far as the coating agent of sole Al$_2$O$_3$.

The present invention has been realized to solve difficulties involved in the prior art.

That is, the invention is to offer a sensor for measuring the amount of oxygen in the molten metal, which avoids cracking of exfoliation at immersion of the coating agent on the surface of the element, and brings about the wave of the measured emf in a short period of time without obstructing the oxygen ion conductivity of the element.

DISCLOSURE OF THE INVENTION

The coating agent according to the invention is not different from the existing one in such a regard that is exhibits the combining force at the room temperature by the organic binder. However, the invention is to increase strength of the coating layer by mixing solely or jointly additive(s) having the strong combination with Al$_2$O$_3$ at the high temperatures.

The additive herein is metallic fluoride taking it into consideration to (1) use water when controlling the coating agent and (2) absorb moisture after incorporation into the sensor, since metallic fluoride is difficult in water dissolution. Metallic fluoride is, for example, CaF$_2$ or MgF$_2$, and the water dissolution thereof is MgF$_2$: 7.6 mg/L (18° C.)
CaF$_2$: 1.6 mg/100 g (18° C.)

If the coating layer is formed by adding the fluoride as such above mentioned, fluoride is oxidized into oxide just after immersion and the layer is made strong by reaction with Al$_2$O$_3$ powder and may display ideal coating effect satisfying the above (1) and (2) items.

BRIEF DESCRIPTION OF THE DRAWINGS

FIGS. 4, 5, 6, 7, 8 and 9 are examples of measuring waves by the sensers according to the present invention;

Figure 1:
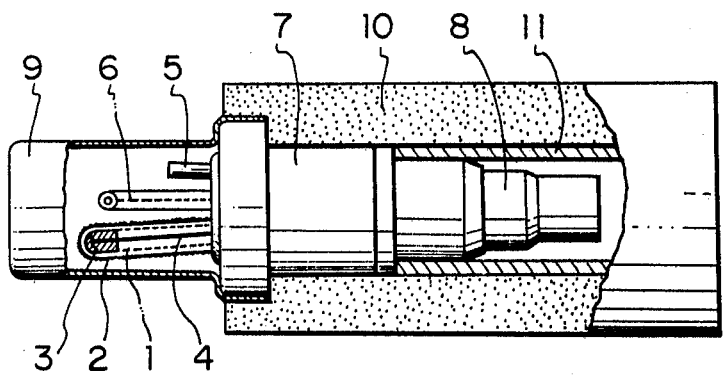
FIG. 1 is an outlined view showing an ordinary structure of the sensor for measuring the density of oxygen in the molten metal.
Figure 2:
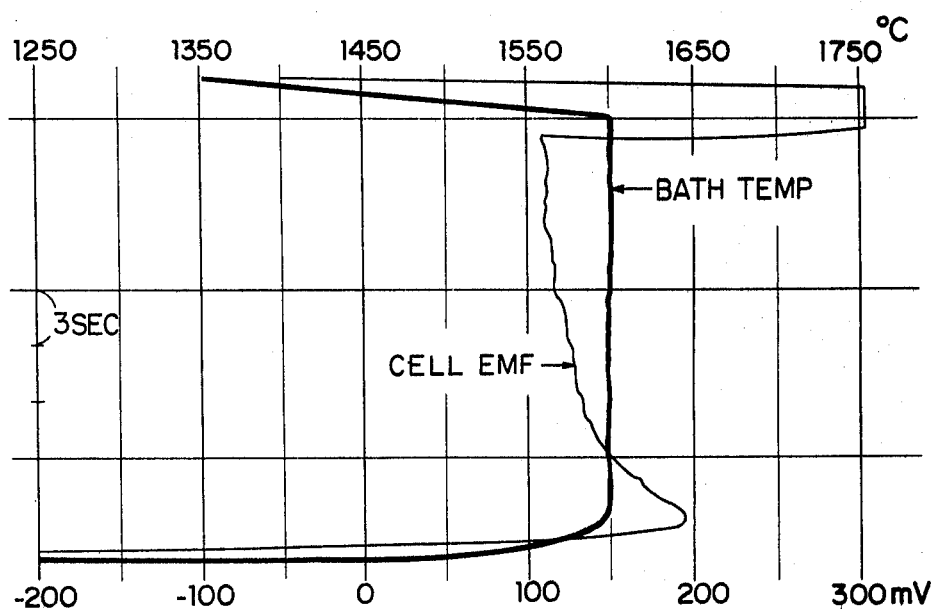
FIG. 2 is an example of measuring wave by the sensor using an element which does not have the coating.

In the drawings, the reference numeral 1 is a solid electrolytic element, and 2 is a coating agent.

EMBODIMENT FOR REDUCING THE INVENTION TO PRACTICE

The invention will be explained in detail in accordance with the embodiment.

[EXAMPLE 1]

Investigations were made to varying of the coating agent immersed into the molten steel.

TABLE 1

| | Mixing condition of coating agents (wt. %) | | | | |
|---|---|---|---|---|---|
| | (a) | | | | |
| (b) | A | B | C | D | E |
| Al$_2$O$_3$ | 60 | 51 | 51 | 51 | 51 |
| MgF$_2$ | 0 | 9 | 6 | 3 | 0 |
| CaF$_2$ | 0 | 0 | 3 | 6 | 9 |
| Organic binder | 3 | 3 | 3 | 3 | 3 |
| Water | 37 | 37 | 37 | 37 | 37 |

(a): Coating agents
(b): Mixing raw materials
A: Conventional products

Raw materials were mixed at proportions shown in Table 1, and water was added to make slurry of 60% in concentration. The slurry was uniformly coated on the surface of ZrO$_2$ (MgO) elements which were closed at one ends. Those were dried by touching to the human fingers and subsequently subjected to drying treatment at temperature of 130° C. for 24 hours, and those elements were immersed into the molten steel by a 20 kg high-frequency induction furnace.

The molten steel was S45C, and the temperatures thereof were 1550° C., 1600° C. and 1650° C. With respect to test results, although fine cracking ran in the coatings B, C, D and E as shown in Table 2, exfoliation did not appear at all as seen in the existing coating agent. It is seen from this fact that improvement is brought about by mixing fluoride additives.

TABLE 2

| | Changings of coating agents after immersion in | | | | |
|---|---|---|---|---|---|
| | (a) | | | | |
| (c) | A | B | C | D | E |
| 1650° C. | X | ○ | ○ | ○ | ◎ |
| | — | ◎ | ○ | △ | △ |
| 1600° C. | X | ○ | ◎ | ◎ | ◎ |
| | — | ◎ | ○ | ○ | △ |
| 1550° C. | △ | ◎ | ◎ | ◎ | ◎ |
| | ◎ | ◎ | ◎ | ○ | △ |

TABLE 2-continued

| | Changings of coating agents after immersion in | | | | |
|---|---|---|---|---|---|
| | (a) | | | | |
| (c) | A | B | C | D | E |

(a): Coating agents
(c): Temperatures of molten steel
A: Conventional products
Upper: Strength of coating layer
◎ Superior
○ Good (No exfoliation but small crakings)
△ Partial exfoliation
X Overall exfoliation
Lower: Bubblings on coated surfaces
◎ Very little bubblings
○ Partial bubbles
△ Overall bubbles In the CaF$_2$ additive coating agents C, D and E, air bubbles (around 0.1 to 0.3 mm in diameter) often appear on their surfaces.

This results because the Al$_2$O$_3$—CaO coating agent generates vitrified compounds of low melting point, those are absorbed in open pores of the element, or the gas made by burning of the binder cannot escape from the surface and the air bubbles remain therein. On the other hand, the Al$_2$O$_3$—MgO coating does not generate such compounds of low melting point and therefore the air bubbles do not remain.

[EXAMPLE 2]

The element having the coating was incorporated into the sensor, and the amount of dissolved oxygen was measured. Table 3 shows the compounding conditions of the coating agents.

The control of the coating agent and the coating manner are the same as in Example 1. PVA (polyvinyl alcohol) was used for the organic binder. Tests were ten times made per each level of carbon to thirty coating agents.

The structures of the senser is the same as in FIG. 1.

TABLE 3

| | Mixing condition of coating agents (wt. %) | | | |
|---|---|---|---|---|
| | (a) | | | |
| (b) | A | F | G | H |
| Al$_2$O$_3$ | 60 | 50 | 50 | 50 |
| MgF$_2$ | 0 | 10 | 5 | 0 |
| CaF$_2$ | 0 | 0 | 5 | 10 |
| Organic binder | 3 | 3 | 3 | 3 |
| Water | 37 | 37 | 37 | 37 |

(a): Coating agent
(b): Mixing raw materials
A: Conventional products
Measuring conditions are as under
Melting furnace   50 Kg high-frequency induction furnace
Melting temp.     1600° C.
Molten steel      Fe—C—O (C: 0.10%, 0.20%, 0.40%)
                  The amount of oxygen in the molten steel was controlled with the amount of adding granular graphite, and the surface of the steel bath was sealed with Ar gas.

Figure 3:
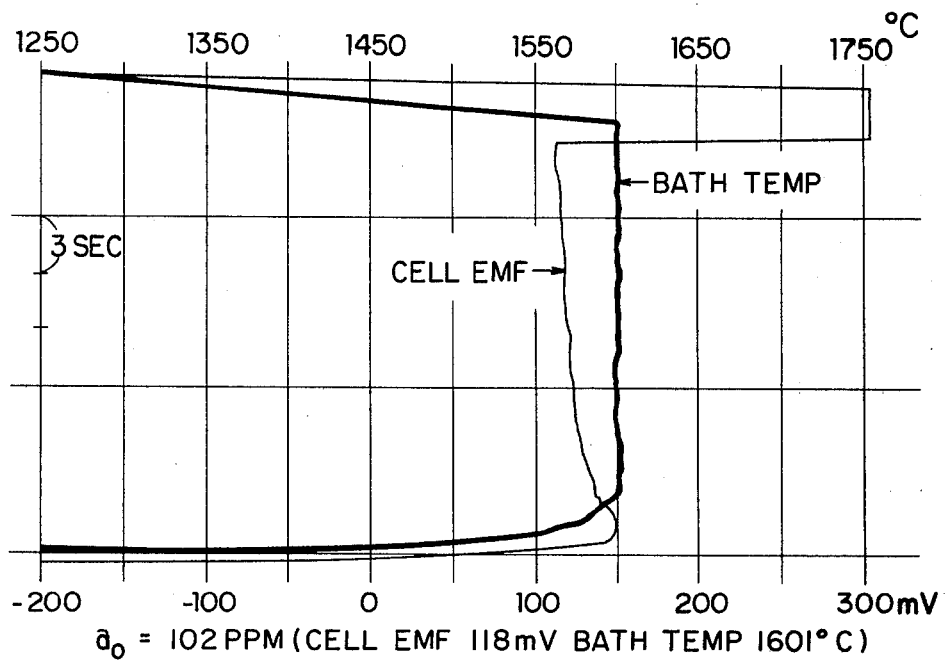
FIG. 3 is an example of measuring wave by the sensor using an element which has the conventional coating.
Figure 4:
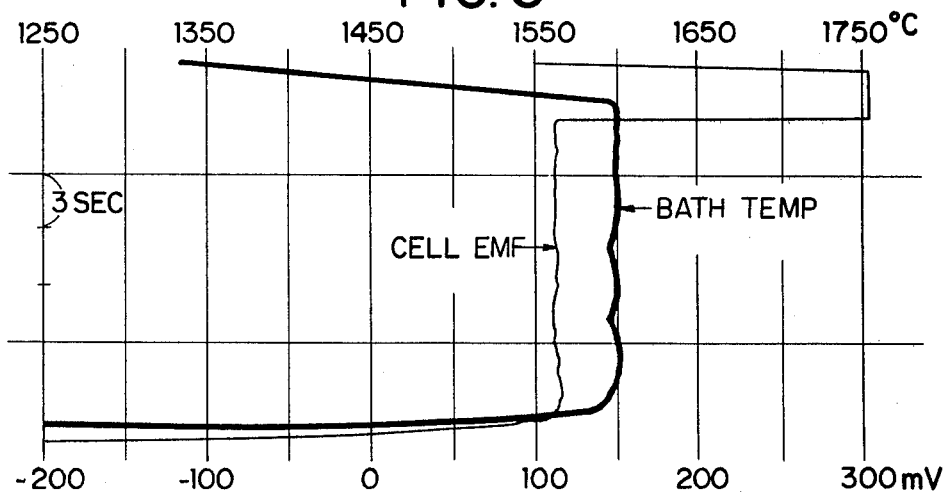
Figure 5:
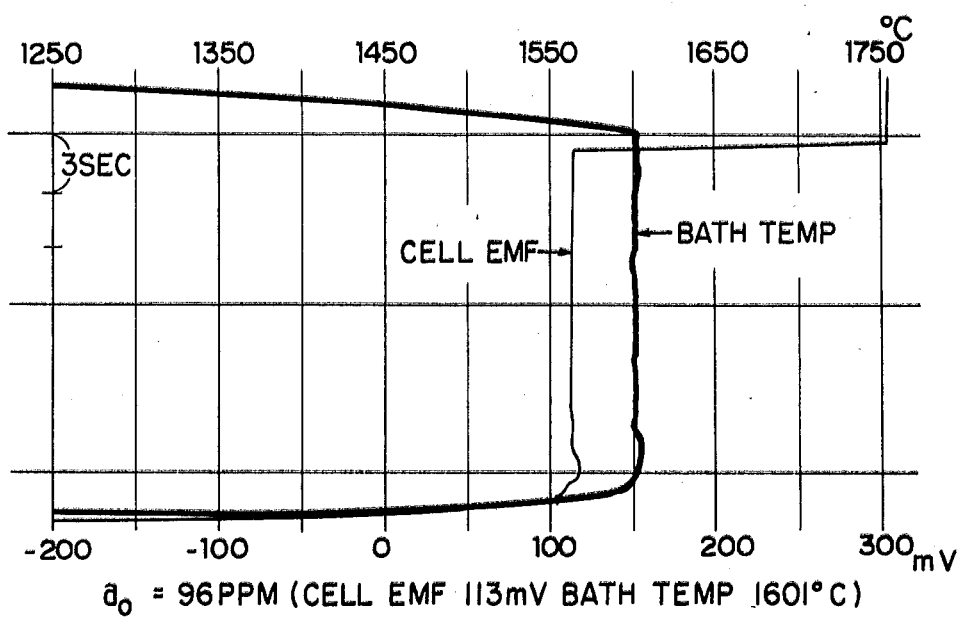
Figure 6:
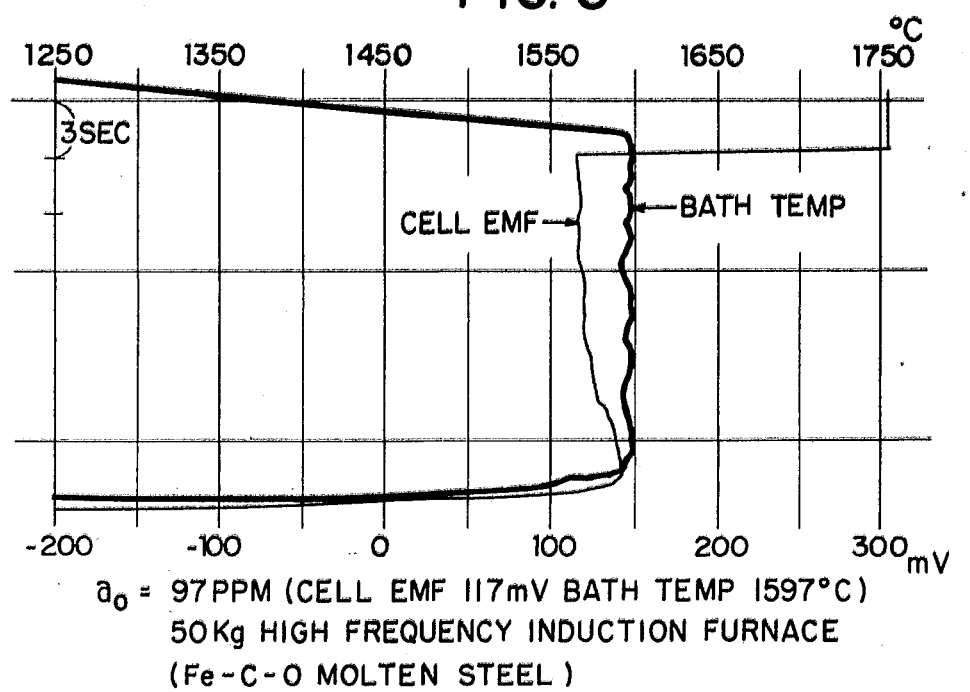

Typical examples of measuring waves are shown in FIGS. 3–6. FIG. 3 is a case using an element coated with the conventional product A, FIG. 4 is a case using an element coated with "F", FIG. 5 is of "G", and FIG. 6 is of "H". Table 4 hereunder shows quantitative appreciation of measured emf waves in accordance with under mentioned classification.

Emf waves are classified in following classes, and are averaged with points 1 to 6. The lesser is the numerical figure, the better is the result.

TABLE 4

Appreciation of measured emf waves

| C content | (a) A | F | G | H |
|---|---|---|---|---|
| 0.10% | 2.9 | 1.9 | 2.0 | 2.6 |
| 0.20% | 4.3 | 1.8 | 2.4 | 3.8 |
| 0.40% | 3.9 | 1.8 | 2.1 | 2.9 |
| (Average) | 3.7 | 1.8 | 2.2 | 3.1 |

| Class | Emf waves | Measuring time | |
|---|---|---|---|
| 1 | Superior | less than 10 sec | |
| 2 | Excellent | 10 to 15 sec. | Longer time than Class 1 |
| 3 | Small disorder | 10 to 15 sec. | Small hunting or vibrations |
| 4 | Increasing, decreasing | 15 to 20 sec | Time is longer, but equilibrium line is drawn |
| 5 | Increasing, decreasing | More than 20 sec | Equilibrium line is not drawn |
| 6 | Fluctuation, vibration | — | |

Classes 5 and 6 are bad waves and are unreadable
(a): Coating agents
A: Conventional products Table 5 shows times until obtaining the average value and the appreciation thereof.

As a result, every case shows improvements of emf waves by addition of metallic fluoride.

TABLE 5

| | Time taken for measuring | | | |
|---|---|---|---|---|
| C content | (a) A | F | G | H |
| 0.10% | 14.2 | 9.4 | 9.8 | 11.9 |
| 0.20% | 18.4 | 8.9 | 9.5 | 15.6 |
| 0.40% | 16.2 | 9.2 | 9.3 | 13.7 |
| (Average) | 16.3 | 9.2 | 9.5 | 13.7 |

(a): Coating agents
A: Conventional products

Since the coating agents according to the invention do not exfoliate at immersion into the molten steel, the effects may be fully expected to bring about satisfactory results. With respect to the measuring time, the coating agents by the invention shorten 5 to 9 seconds than the conventional products as is seen in Table 5. In the steel making field, the work at the high temperatures may be reduced.

The coating agent H is more or less smaller in improvement than the other coating agents, and this is assumed to be related to the occurrence of the air bubbles having been mentioned in Example 1. In regard to $Al_2O_3$—CaO, this is assumed to depend upon the decreasing and increasing tendencies taking longer time until obtaining the equilibrium line of emf wave, since the vitrified compound of low melting point hinders dispersion of oxygen at the boundary of the molten steel and the element.

[EXAMPLE 3]

Test results of the immersion at the steel making field are shown. The sensor has the same structure as shown in FIG. 1. The mixing condition of the coating agents are shown in Table 6.

TABLE 6

| Mixing condition of coating agents (wt. %) | | |
|---|---|---|
| (b) | (a) I | J |
| $Al_2O_3$ | 42 | 42 |
| $MgF_2$ | 18 | 15 |
| $CaF_2$ | 0 | 3 |
| Organic binder | 3 | 3 |
| Water | 37 | 37 |

(a): Coating agents
(b): Mixing raw materials

The measured waves are shown in FIGS. 7 to 9.

Figure 10:
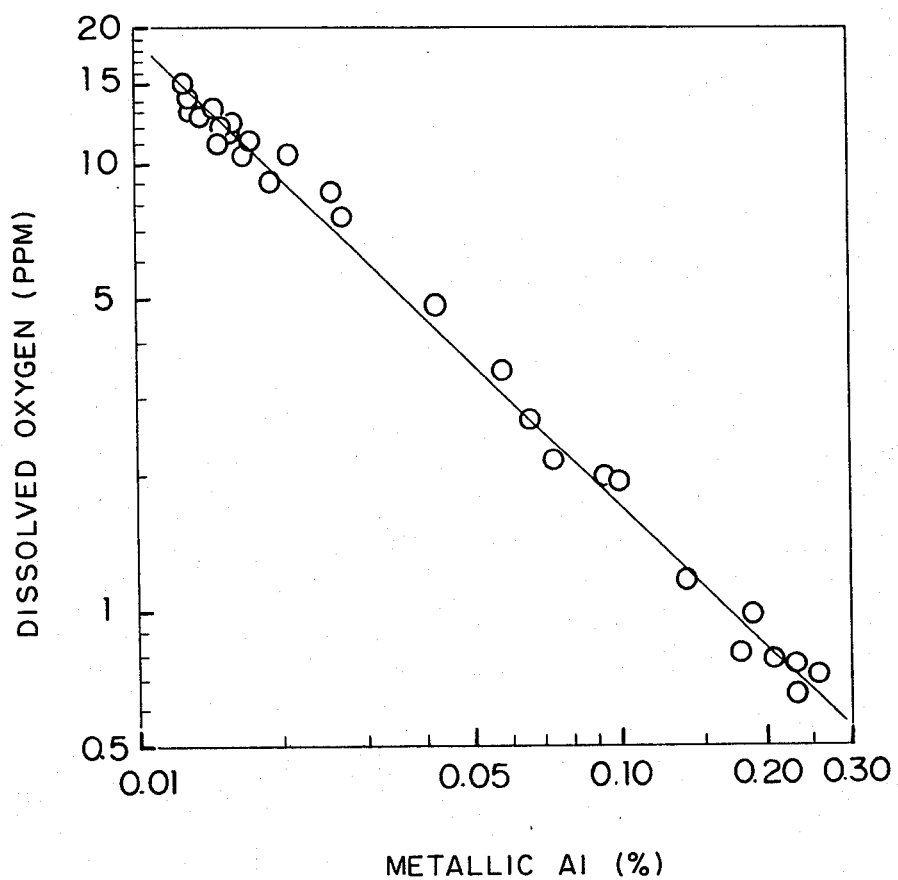
FIG. 10 is a graph showing interrelation between the amount of measuring molten oxygen and the amount of metallic Al.
Figure 11:
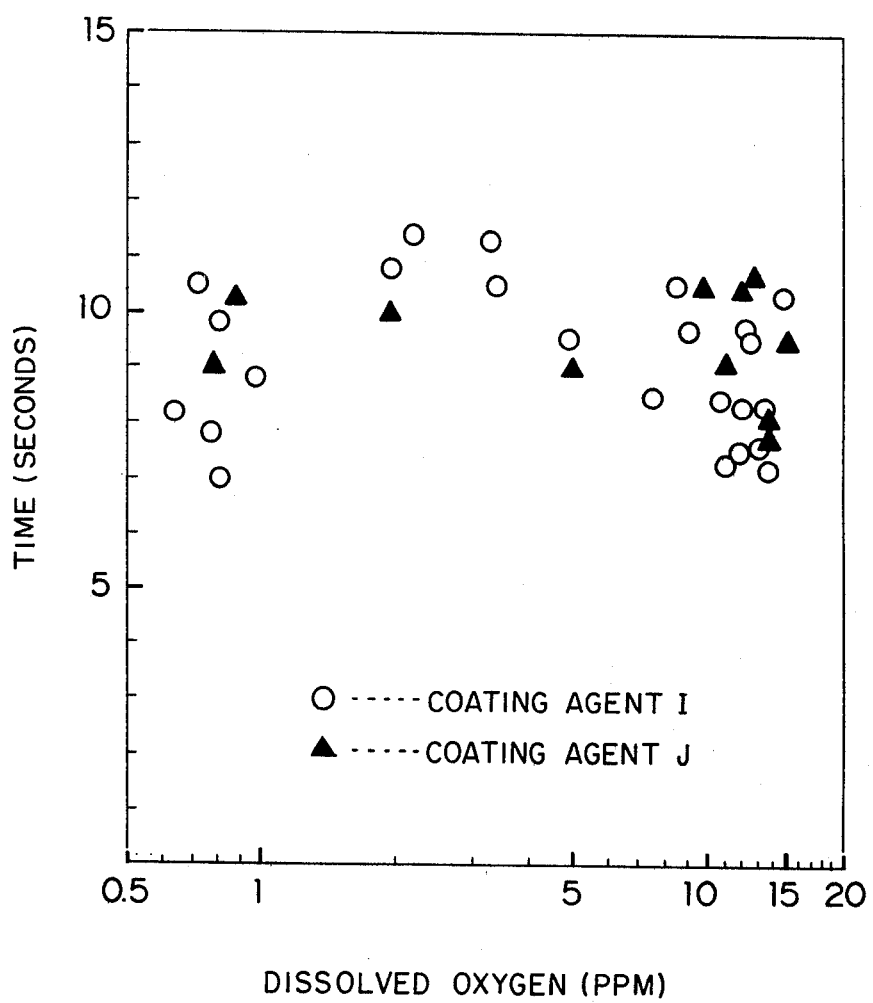
FIG. 11 is a graph showing relation between the amount of measuring molten oxygen and time taken for measuring.

FIG. 7 is the measured wave (coating agent I) of the molten steel in the 300 ton ladle just after teeming from the converter, FIGS. 8 and 9 are the measured waves (FIG. 8: coating agent I, and FIG. 9: coating agent J) of the molten metal in the 250 ton ladle during the RH degassifying treatment, and the measured steels are Al killed steel. FIG. 10 show interrelation between the amount of dissolved oxygen obtained by the measuring in the RH degassifying apparatus and the amount of metallic Al (sol.Al) obtained by the analysis of the sample at the same time. FIG. 11 shows the relationship between the amount of dissolved oxygen and the time required to measure. Each of the other cases shows that the same improvement as the invention could be obtained in the measurings of the steel making field, too.

INDUSTRIAL APPLICABILITY

As can be seen from the above discussion, a sensor according to the invention is used to measuring the amount of dissolved oxygen in the molten metal such as the molten steel, copper and others, especially is suited to such cases requiring said measuring in a short period of time at the high temperatures used in the steel making field.

We claim:

1. In an oxygen sensor for measuring the oxygen content of molten metal comprising a solid ion conductive electrolyte having an inner and an outer surface, said solid electrolyte having a protective coating containing a binding agent on the outer surface thereof intended to be immersed in the molten metal being measured,
   the improvement comprising said protective coating containing powders of at least one metallic fluoride.

2. The sensor of claim 1, wherein said protective coating comprises $Al_2O_3$.

3. The sensor of claim 1, wherein said binder is an organic binder.

4. The sensor of claim 3, wherein said organic binder is polyvinyl alcohol.

5. The sensor of any one of claims 1, 3 or 4 containing at least one fluoride selected from the group consisting of $MgF_2$ and $CaF_2$.

6. The sensor of claim 3, wherein said protective coating contains $Al_2O_3$ and at least one fluoride selected from the group consisting of $MgF_2$ and $CaF_2$.

7. The sensor of claim 6 containing between 42 and 60 parts of $Al_2O_3$.

8. The sensor of claim 7 containing between 0 and 18 parts of $MgF_2$ and between 0 and 10 parts of $CaF_2$.

9. The sensor of claim 8 containing between 3 and 18 parts of $MgF_2$.

10. The sensor of claim 9 containing between 3 and 10 parts of $CaF_2$.

11. The sensor of any one of claims 7, 8, 9 or 10 containing polyvinyl alcohol as the binding agent.

* * * * *